(12) United States Patent
Anderhub et al.

(10) Patent No.: US 8,709,040 B2
(45) Date of Patent: Apr. 29, 2014

(54) SUTURE ANCHOR, GUIDE FOR LOCATING A HOLE IN A BONE, AND SUTURE ANCHOR DELIVERY TOOL

(75) Inventors: Otto E. Anderhub, Miami, FL (US); Sigfrido Delgado, Aventura, FL (US); Luis A. Diaz, Yabucoa, PR (US)

(73) Assignee: VitaSynergies, LLC, Miami, FL (US)

( * ) Notice: Subject to any disclaimer, the term of this patent is extended or adjusted under 35 U.S.C. 154(b) by 801 days.

(21) Appl. No.: 12/492,822

(22) Filed: Jun. 26, 2009

(65) Prior Publication Data
US 2009/0326579 A1 Dec. 31, 2009

Related U.S. Application Data

(60) Provisional application No. 61/133,124, filed on Jun. 26, 2008.

(51) Int. Cl.
*A61B 17/04* (2006.01)
(52) U.S. Cl.
USPC ........................................................... 606/232
(58) Field of Classification Search
USPC ............. 606/75, 95, 219, 232, 265, 300, 304, 606/151–158
See application file for complete search history.

(56) References Cited

U.S. PATENT DOCUMENTS

| | | | |
|---|---|---|---|
| 5,100,418 A | 3/1992 | Yoon et al. | |
| 5,154,719 A | 10/1992 | Cotrel et al. | |
| 5,167,664 A | 12/1992 | Hodorek | |
| 5,658,313 A | 8/1997 | Thal | |
| 5,957,953 A * | 9/1999 | DiPoto et al. | 606/232 |
| 5,993,459 A | 11/1999 | Larsen et al. | |
| 6,254,632 B1 | 7/2001 | Wu et al. | |
| 6,527,794 B1 | 3/2003 | McDevitt et al. | |
| 6,689,153 B1 | 2/2004 | Skiba | |
| 6,855,157 B2 | 2/2005 | Foerster et al. | |
| 7,396,539 B1 | 7/2008 | Hossainy et al. | |
| 2003/0069605 A1* | 4/2003 | Bonutti et al. | 606/232 |
| 2003/0078604 A1* | 4/2003 | Walshe | 606/151 |
| 2005/0055052 A1 | 3/2005 | Lombardo et al. | |
| 2005/0245932 A1* | 11/2005 | Fanton et al. | 606/72 |
| 2006/0116719 A1 | 6/2006 | Martinek | |
| 2006/0222756 A1 | 10/2006 | Davila et al. | |
| 2006/0282083 A1 | 12/2006 | Fanton et al. | |
| 2007/0073342 A1 | 3/2007 | Stone et al. | |
| 2007/0260259 A1 | 11/2007 | Fanton et al. | |

(Continued)

*Primary Examiner* — Ryan Severson
*Assistant Examiner* — Katherine M Shi
(74) *Attorney, Agent, or Firm* — Laurence A. Greenberg; Werner H. Stemer; Ralph E. Locher (57) ABSTRACT

A suture anchor includes two clamping surfaces that secure one or more suture strands between them. Cooperating engaging structures, such as recesses and a projection enable the clamping surfaces to be incrementally moved closer together such that the force applied between the clamping surfaces is increased in predetermined increments to secure the suture strands. If the applied force is too high, the clamping surfaces can be released from a fixed position, and the force applied by the clamping surfaces can again be incrementally increased to the desired clamping force. A guide is provided to mark the location of the hole that has been drilled in the bone. A suture anchor delivery tool is provided to insert and secure the suture anchor in the hole in the bone. The suture anchor delivery tool enables the surgeon to move the clamping surfaces of the suture anchor towards each other.

12 Claims, 12 Drawing Sheets

(56) References Cited

U.S. PATENT DOCUMENTS

| | | |
|---|---|---|
| 2007/0270907 A1 | 11/2007 | Stokes et al. |
| 2007/0276437 A1 | 11/2007 | Call et al. |
| 2008/0009904 A1 | 1/2008 | Bourque et al. |
| 2008/0033486 A1 | 2/2008 | Whittaker et al. |
| 2008/0086138 A1 | 4/2008 | Stone et al. |
| 2008/0109037 A1 | 5/2008 | Steiner et al. |
| 2008/0154260 A1 | 6/2008 | Hoof |
| 2010/0004683 A1* | 1/2010 | Hoof et al. .................. 606/232 |

* cited by examiner

SUTURE ANCHOR, GUIDE FOR LOCATING A HOLE IN A BONE, AND SUTURE ANCHOR DELIVERY TOOL

CROSS-REFERENCE TO RELATED APPLICATION

This application claims the benefit under 35 U.S.C. §119 (e) of our provisional application No. 61/133,124 filed Jun. 26, 2008. As far as possible under the rules, the prior application is herewith entirely incorporated by reference.

BACKGROUND OF THE INVENTION

1. Field of the Invention

The invention relates to a suture anchor, a guide for locating a hole in a bone, a suture anchor delivery device, and a therapeutic agent delivery device.

2. Description of the Related Art

It is known to use a suture anchor to attach soft tissue, such as a tendon or a ligament, to a bone. A surgeon drills a hole in the bone and secures the suture anchor in the hole in the bone. A suture is attached to the soft tissue and the suture is typically secured to an eyelet of the suture anchor using a knot.

BRIEF SUMMARY OF THE INVENTION

It is an object of the invention to provide a suture anchor that does not require the surgeon to use a knot in order to secure one or more suture strands to a suture anchor. It is an additional object of the invention to provide a suture anchor that enables the surgeon to increase the force applied between two clamping surfaces in predetermined increments. These clamping surfaces are used to secure one or more suture strands between them. When the clamping surfaces are in the desired position, they are fixed in that position so that the desired force is applied between the clamping surfaces to secure the one or more suture strands in the suture anchor. A further object of the invention is to enable the clamping surfaces of the suture anchor to be released from a fixed position in which one or more suture strands are secured between the clamping surfaces. The feature enabling the clamping surfaces to be released from a fixed position provides the surgeon with the ability to repeat the process used to incrementally move the clamping members together and to thereby incrementally increase the force applied between two clamping surfaces so that the desired force can be applied to secure the suture strand(s) between the clamping surfaces.

It is another object of the invention to provide a guide that can be used by a surgeon to mark the location of the hole that has been drilled in the bone. This makes it easier for the surgeon to locate the hole in order to perform a subsequent procedure, such as, securing a suture anchor in the hole.

It is another object of the invention to provide a suture anchor delivery tool that can be used to insert and secure the suture anchor in the hole in the bone. Preferably the suture anchor delivery tool is also constructed to enable the surgeon to move the clamping surfaces of the suture anchor towards each other. In this manner, the suture anchor delivery tool enables the surgeon to adjust the force applied between the clamping surfaces of the suture anchor in order to properly secure one or more suture strands between the clamping surfaces.

It is another object of the invention to provide a therapeutic agent delivery device that includes a member with a surface suitable for receiving a therapeutic agent and for delivering the therapeutic agent to living tissue.

With the foregoing and other objects in view there is provided, in accordance with the invention, a suture anchor including a suture anchor body for placement in a bone. The suture anchor body is formed with a cavity and a first clamping surface. The suture anchor also includes a securing member constructed to be at least partially received in the cavity of the suture anchor body. The securing is member formed with a second clamping surface. The suture anchor body and the securing member cooperate to define a passage between the first clamping surface and the second clamping surface for receiving at least one suture strand. The suture anchor body and the securing member are formed with cooperating engaging structures enabling a distance between the first clamping surface and the second clamping surface to be adjusted and fixed in predetermined increments.

With the foregoing and other objects in view there is also provided, in accordance with the invention, a guide for marking or locating a hole in a bone. The guide includes a hollow cylindrical body sized for insertion into the hole in the bone and sized for receiving a suture anchor body. The cylindrical body includes an end formed with a flange having a surface. The guide can include a radiopaque material. The guide can additionally or alternatively include a surface to which a therapeutic agent can be applied in order to deliver the therapeutic agent to living tissue.

With the foregoing and other objects in view there is also provided, in accordance with the invention, a therapeutic agent delivery device including a member with a surface suitable for receiving a therapeutic agent and for delivering the therapeutic agent to living tissue. The surface of the therapeutic agent delivery platform is formed with an aperture sized for receiving the cylindrical body of the guide that locates the hole in the bone.

With the foregoing and other objects in view there is also provided, in accordance with the invention, a suture anchor delivery tool that includes a handle portion, and a plurality of prongs that extend from the handle portion. The actual number of prongs could be two or more. At least two of the prongs include an end with a protuberance configured to secure a suture anchor. The suture anchor delivery tool also includes an actuating member disposed in the handle portion. The actuating member is configured to move the protuberances of the prongs towards or away from each other. The actuating member includes an end formed with a structure configured to mate with a turning device of an anchor. The actuating member is rotatably disposed in the handle portion. The actuating member is longitudinally movably disposed in the handle portion such that the end of the actuating member is moveable towards and away from the ends of the prongs.

Other features which are considered as characteristic for the invention are set forth in the appended claims.

Although the invention is illustrated and described herein as embodied in a suture anchor, a guide for locating a hole in a bone, a suture anchor delivery device, and a therapeutic agent delivery device, it is nevertheless not intended to be limited to the details shown, since various modifications and structural changes may be made therein without departing from the spirit of the invention and within the scope and range of equivalents of the claims.

The construction of the invention, however, together with additional objects and advantages thereof will be best understood from the following description of the specific embodiment when read in connection with the accompanying drawings.

DESCRIPTION OF THE PREFERRED EMBODIMENTS OF THE INVENTION

The exemplary embodiments described herein are merely given as examples of ways in which the inventive concept can be implemented. The invention should not be construed as being limited to any particular exemplary embodiment or to any particular feature of an exemplary embodiment. Rather the exemplary embodiments are provided merely as examples of ways in which the inventive concept disclosed herein can be implemented.

Figure 1:
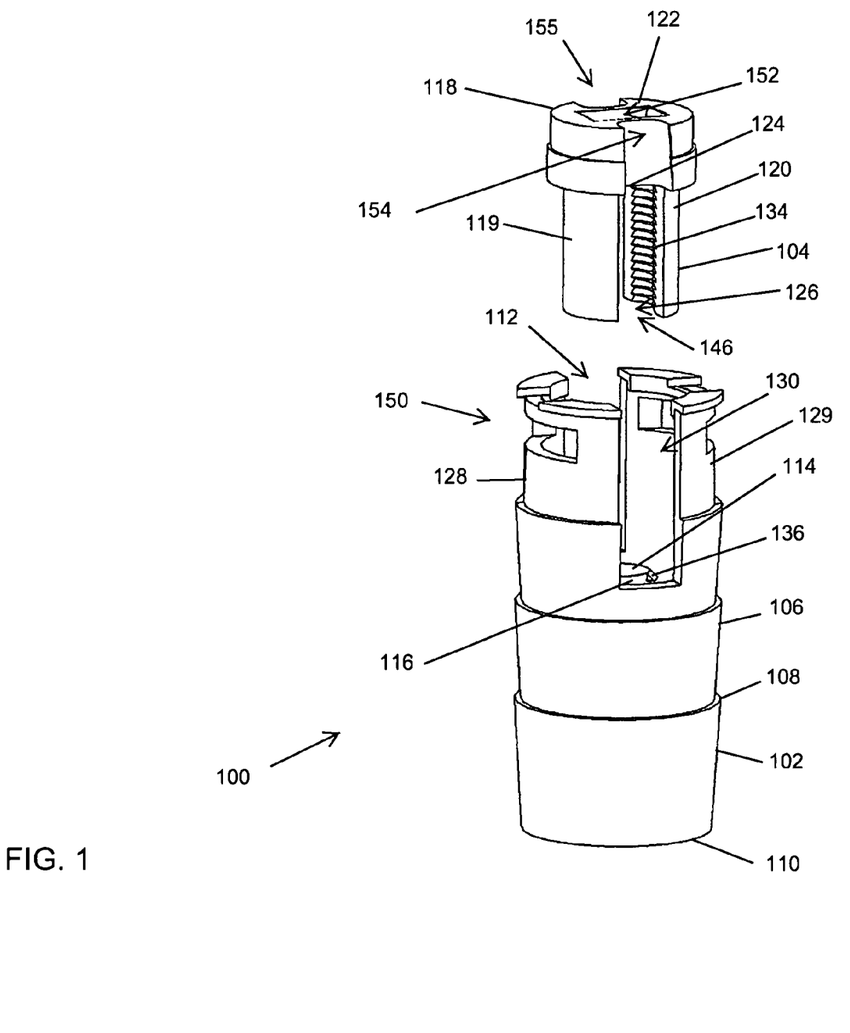
FIG. 1 is an exploded perspective view of an exemplary embodiment of a suture anchor.

Referring now to the figures of the drawing in detail and first, particularly, to FIG. 1 thereof, there is shown an exploded view of an exemplary embodiment of a suture anchor 100 that includes a suture anchor body 102 and a securing member 104. The suture anchor body 102 extends in a longitudinal direction. The suture anchor body 102 is constructed with an outer surface 106 that is configured to be introduced in a hole that is made in a bone. The outer surface 106 can include structures for forming an interference fit with the surface of the bone in the hole. One example of such a structure is a ridge 108; however other types of structures could also be used. The outer surface 106 could alternatively include threads for forming a screw-type fit with the bone. The suture anchor body 102 is preferably cylindrical in shape and has a lower end 110 that is preferably closed. The lower end 110 is the end that will be placed in the hole of the bone to the furthest extent. The suture anchor body 102 is formed with a cavity 112 and a first clamping surface 114 is formed in the cavity 112. The first clamping surface 114 serves as one half of a clamping structure used to clamp or secure one or more suture strands. This will be explained in more detail below. One possible way of constructing the first clamping surface 114 is to form an inner guide post 116 that extends upward from the surface 140 (see FIG. 3), which is inside the cavity 112, at the lower end 110. The top surface of this inner guide post 116 then forms the first clamping surface 114.

The securing member 104 is constructed to be at least partially received in the suture anchor body 102, and is preferably constructed to be fully received in the suture anchor body 102 when the suture strand or strands are secured. The securing member 104 extends in the same longitudinal direction as does the suture anchor body 102. The securing member 104 may be constructed to include a top portion 118 and at least two prongs or legs 119, 120 that extend from the top portion 118. The top portion 118 includes a top surface 122 and a bottom surface that is opposite the top surface 122. The region of the bottom surface that is between the legs 119, 120 forms a second clamping surface 124.

Figure 2:
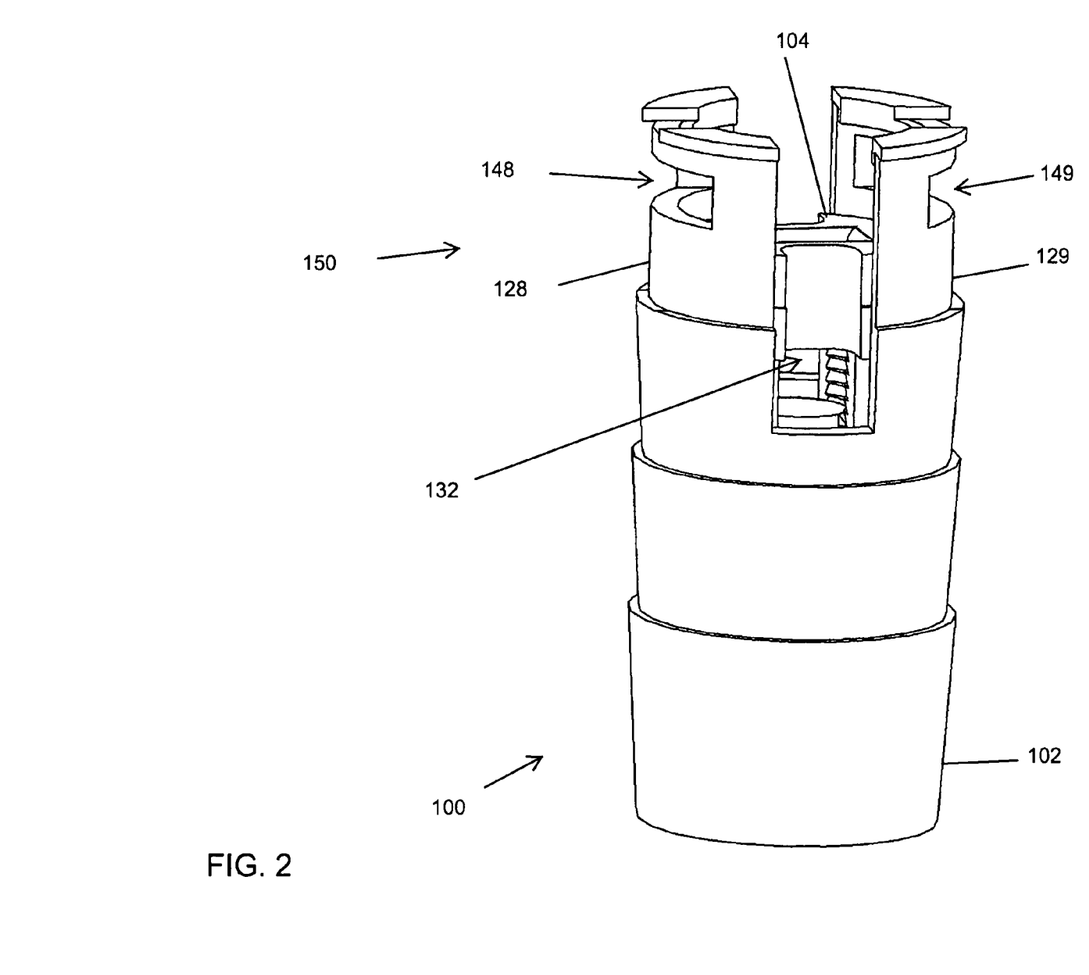
FIG. 2 is a perspective view of the exemplary embodiment of the suture anchor.

The region between the two legs 119, 120 of the securing member 104 forms a space 126 that transversely extends completely through the securing member 104. The upper end portion 150 of the suture anchor body 102 may be constructed to include at least two extensions or arms 128, 129 that extend away from the main portion of the suture anchor body 102. The region between the two arms 128, 129 forms a space 130 that transversely extends completely through the suture anchor body 102. When the securing member 104 is received in the cavity 112 of the suture anchor body 102 as shown in FIG. 2, the space 126, which transversely extends completely through the securing member 104, and the space 130, which transversely extends completely through the suture anchor body 102, cooperate to define a channel or passage 132 that completely transversely extends through the suture anchor 100 between the first clamping surface 114 of the suture anchor body 102 and the second clamping surface 124. One or more suture strands will be routed through the passage 132 and will be secured between the first clamping surface 114 and the second clamping surface 124 by a clamping force that the first clamping surface 114 and the second clamping surface 124 applies to the one or more suture strands.

The relative distance between the first clamping surface 114 and the second clamping surface 124 can be adjusted in order to adjust the force that is applied between the clamping surfaces 114, 124 and to the suture strand(s) that are led through the passage 132 between the clamping surfaces 114, 124. This relative distance can advantageously be adjusted in predetermined increments. With the benefit of the disclosure herein one of ordinary skill in the art should now be enabled to construct many different types of mechanisms that will enable the force applied between two clamping surfaces 114, 124 to be adjusted. The particular mechanism described herein for moving the clamping surfaces 114, 124 together is merely given as an example and should not be construed as limiting the scope of the invention.

The suture anchor body 102 and the securing member 104 are formed with cooperating engaging structures that enable the distance between the first clamping surface 114 and the second clamping surface 124 to be adjusted and fixed in predetermined increments. The cooperating engaging structures could be made of non-ferrous materials to prevent movement and potential loosening during magnetic imaging procedures. In the exemplary embodiment described herein, the cooperating engaging structures are recesses 134, which are formed between a plurality of teeth, and a projection 136 that fits between the teeth and in the recesses 134. It should be understood that other types of cooperating engaging structures could be used, and the invention should not be construed as being limited to using recesses and a projection. In the exemplary embodiment, the projection 136 is formed on the circumferential surface of the inner guide post 116 near the first clamping surface 114, and the plurality of teeth and the recesses 134, which are between the teeth, are formed on the inner surfaces of the legs 119, 120. It is also possible to change the exact locations of the securing member 104 at which the recesses 134 are formed and to change the exact location of the suture anchor body 102 at which the projection 136 is formed. Additionally, the locations of the recesses 134 and the projection 136 could be reversed such that recesses are formed on some part of the securing member 104 and a projection is formed on some part of the suture anchor body 102.

A disengagement channel 146 may also be formed to enable the projection 136 to be disengaged from the recess 134 that is holding or mating with the projection. As an example, the disengagement channel 146 may be formed between the two legs 119, 120 of the securing member 104. If the securing member 104 is rotated along its longitudinal axis or more specifically around the inner guide post 116, the projection 136 will move sideways until it is no longer held in a recess 134. Since the projection 136 is no longer held in a recess 134, the securing member 104 and more specifically the second clamping surface 124 of the securing member 104 is released from the position that was fixed by the recess 134. The second clamping surface 124 of the securing member 104 can then be moved away from the first clamping surface 114 of the suture anchor body 102.

Figure 3:
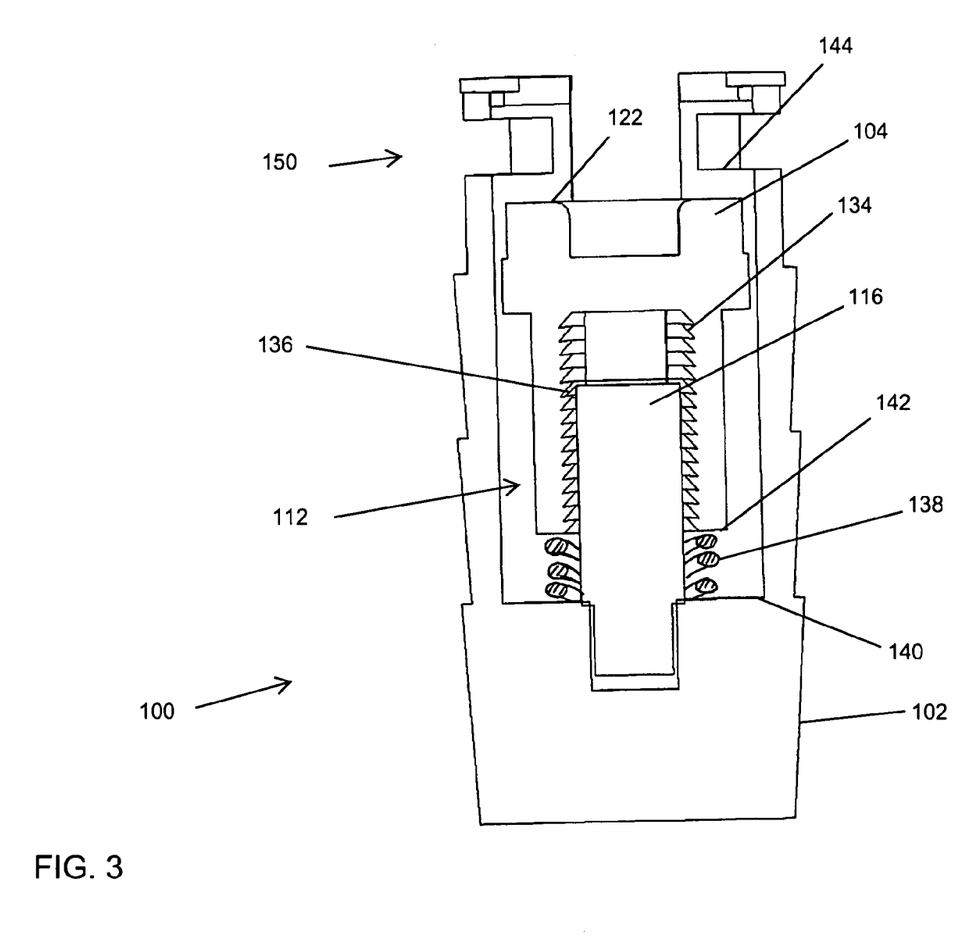
FIG. 3 is a cross sectional view of the exemplary embodiment of the suture anchor.

FIG. 3 is a cross sectional view of the exemplary embodiment of the suture anchor 100. A spring or biasing member 138 may be provided to apply a biasing force between the surface 140 that is inside the cavity 112 of the suture anchor body 102 and the bottoms 142 of the legs 119, 120 of the securing member 104. The biasing member 138 will apply a biasing force that moves the securing member 104 away from the suture anchor body 102 when the projection 136 is moved into the disengagement channel 146. The biasing member 138 also applies an opposing pressure when securing member 104 is incrementally moved further into the suture anchor body 102 and the projection 136 enters another recess 134. There are many ways in which the biasing member could be implemented. To give just one example, the biasing member 138 could be implemented as a plurality of resilient inclined washers, known as Belleville washers, which are placed around the inner guide post 116 and which are oriented in an opposing manner. The term "Belleville washer" is known to specify a washer in which the inner surface of the washer, which defines the hole, is raised or lowered with respect to the outer circumferential surface of the washer. The term "opposing manner" is meant to specify that the inner surfaces of the two adjacent Belleville washers will touch, and that the outer circumferential surface of a Belleville washer above or of a Belleville washer below the two adjacent Belleville washers will touch the outer circumferential surface of one of the two adjacent Belleville washers.

As shown in FIG. 3, the upper end portion 150 of the suture anchor body 102 may also include a retaining flange 144 that serves to retain the securing member 104 in the cavity 112 of the suture anchor body 102. If the projection 136 is moved into the disengagement channel 146, the biasing member 138 can only push the securing member 104 away until the top surface 122 of the securing member 104 contacts the retaining flange 144. This prevents the securing member 104 from possibly being separated from the suture anchor body 102 during a surgical procedure.

As can be seen in FIG. 2, the upper end portion 150 of the suture anchor body 102 may also be formed with opposing apertures 148, 149 that can interlock with a complementary shaped structure of a tool. This tool and process will be described in more detail below. As can be seen in FIG. 1, the securing member 104 may be provided with a turning device 152 that can be used to turn the securing member 104 so that the projection 136 is moved into and out of the disengagement channel 146. It is possible to construct the turning device 152 as any structural element that allows the securing member 104 to be turned. For example, the turning device 152 could be a projection that could be grabbed and turned using an appropriate structure of a tool. In the exemplary embodiment, the turning device 152 is implemented as a recess that is formed in the top surface 122 of the securing member 104. A tool can be constructed with a structure that mates with the turning device 152, which in this example, is a recess.

As can be seen in FIG. 1, the securing member 104 can be formed with one or more indented suture passages 154, 155 that extend in the longitudinal direction. The suture passages 154, 155 are constructed for routing one or more suture strands away from the suture anchor body 102 and away from the securing member 104 and for preventing contact between the suture strand(s) and the bone when the suture anchor body 102 is placed in the bone.

Figure 4:
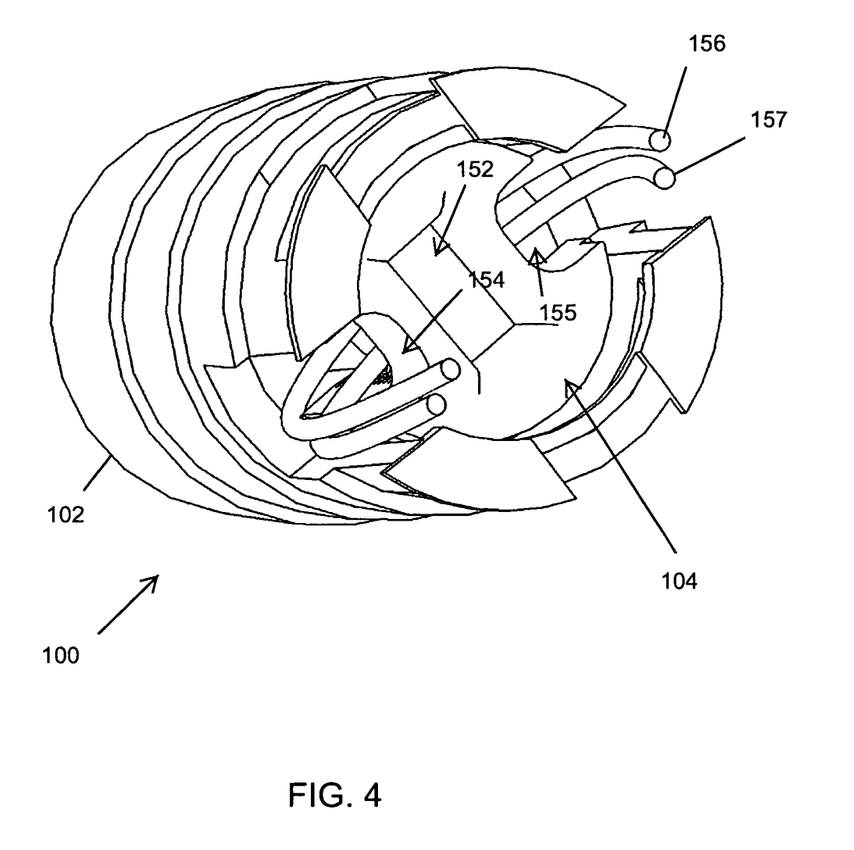
FIG. 4 is another perspective view of the exemplary embodiment of the suture anchor.

FIG. 4 is another perspective view of the exemplary embodiment of the suture anchor 100. Two suture strands 156, 157 are shown extending out of the suture passages 154, 155 of the securing member 104. Since the suture passages 154, 155 enable the suture strands 156, 157 to be pulled entirely within the outer circumferential surface of the suture anchor body 102, frictional contact between the bone and the suture strands 156, 157 is prevented and this eliminates the possibility that the bone may undesirably deteriorate or wear the suture strands 156, 157. The turning device 152 can also clearly be seen in this view.

The suture anchor body 102 and perhaps the securing member 104 may be provided with one or more agents serving various purposes. Such agents include a bonding agent for cells, molecules, and/or proteins, an agent serving as a moisture and chemical barrier, an agent that enables dry lubricity, and/or an agent that prevents fluid conduction of galvanic charge.

The suture anchor 100 including the suture anchor body 102, the securing member 104, and any additional components could be made of bio-absorbable polymers, metal, other non-toxic materials, or any combination of such materials. The suture strands 156, 157 will first be threaded through living tissue, such as, a tendon or a ligament that will be re-attached to a bone. The suture strands 156, 157 will then be lead through the passage 132 of the suture anchor 100. The surgeon can apply the appropriate tension to the suture strands 156, 157, which are routed through the passage 132, in order to bring the living tissue close to the suture anchor 100 and thereby close to the bone. While the appropriate tension is being applied, the surgeon will then incrementally press the securing member 104 further and further inside the cavity 112 of the suture anchor body 102 until the appropriate securing force is applied to the suture strands 156, 157 by the first clamping surface 114 and the second clamping surface 124 in order to secure the suture strands 156, 157 in the suture anchor 100. This will enable the desired tissue apposition to the bone.

Indentations, which could have a semicircular cross section, could be formed in the first clamping surface 114 and/or the second clamping surface 124. These indentations would assist in securely clamping the suture strands 156, 157.

Figure 5:
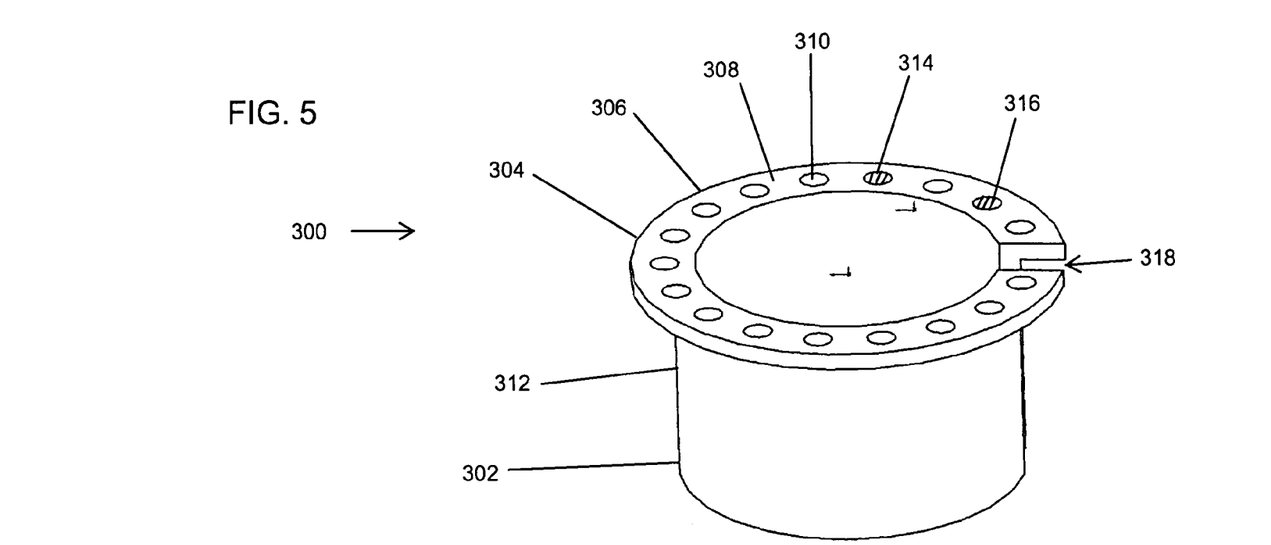
FIG. 5 is a perspective view of an exemplary embodiment of a guide for locating a hole in a bone.

FIG. 5 is a perspective view of an exemplary embodiment of a guide 300 for locating a hole in a bone. The guide 300 includes a hollow cylindrical body 302 that is sized for insertion into the hole in the bone and that is sized for receiving a suture anchor body, for example, the suture anchor body 102 of the suture anchor 100. The cylindrical body 302 includes an end 304 that is formed with a flange 306 having a surface

308. A plurality of apertures 310 may be formed in the flange 306. The cylindrical body 302 is made of a first material 312. A second material 314, which has a greater radiopacity than the first material 312 of the cylindrical body 302, can be affixed to, or can somehow be made a part of the cylindrical body 302 and/or the flange 306. The greater or enhanced radiopacity of the second material 314 enables the exact location of the guide 300 to be determined by using an imaging source such as an x-ray. One option is to affix the second material 314 to the surface 308 of the flange 306. This could be accomplished by filling the surfaces that define the apertures 310 with the second material 314. Alternatively, the apertures 310 could be filled with the second material 314 as shown by the cross-hatching in FIG. 5.

Another option is to use the cylindrical body 302 and/or the flange 306 to deliver one or more drugs or other therapeutic agents 316. A coating of a conformable mix or layers of multiple drugs or therapeutic agents 316 could be applied to the cylindrical body 302 and/or the flange 306. The drugs or therapeutic agents 316 can be affixed to, can coat, or can somehow be made a part of the cylindrical body 302 and/or the flange 306. The drugs or other therapeutic agents 316 will be delivered to the bone and/or other living tissue. The surface 308 of the flange 306 may be coated with one or more drugs or other therapeutic agents 316. One possibility is to coat the surfaces that define the apertures 310 with the drugs or therapeutic agents 316. Another option is to fill the apertures 310 with the drugs or therapeutic agents 316 as shown by the cross hatching in FIG. 5. The cylindrical body 302 could be formed with a slot 318 that enables the size of the outer circumferential surface to be adjusted somewhat. This can assist in fitting the cylindrical body 302 in the hole in the bone.

The plurality of apertures 310 could be constructed with a plurality of different diameters; i.e. they need not all be the same size. The guide 300 can be designed and built in any type of configuration, such as press fit, head linear, renewable, serrata groove, diamond groove, fluid groove, and fluid fill. The cylindrical body 302 could have an internal or external thread, and could be designed to conform to holes of several different diameters. The guide 300 could be made of an expandable material, including, but not limited to polymers, shape memory polymers or alloy, and stainless steel. The guide 300 could be made from a mesh or from woven fibers. The guide 300 could also be coated with agents such as bonding agents, drug release control agents, moisture barriers, chemical barriers, and lubricity.

Figure 6:
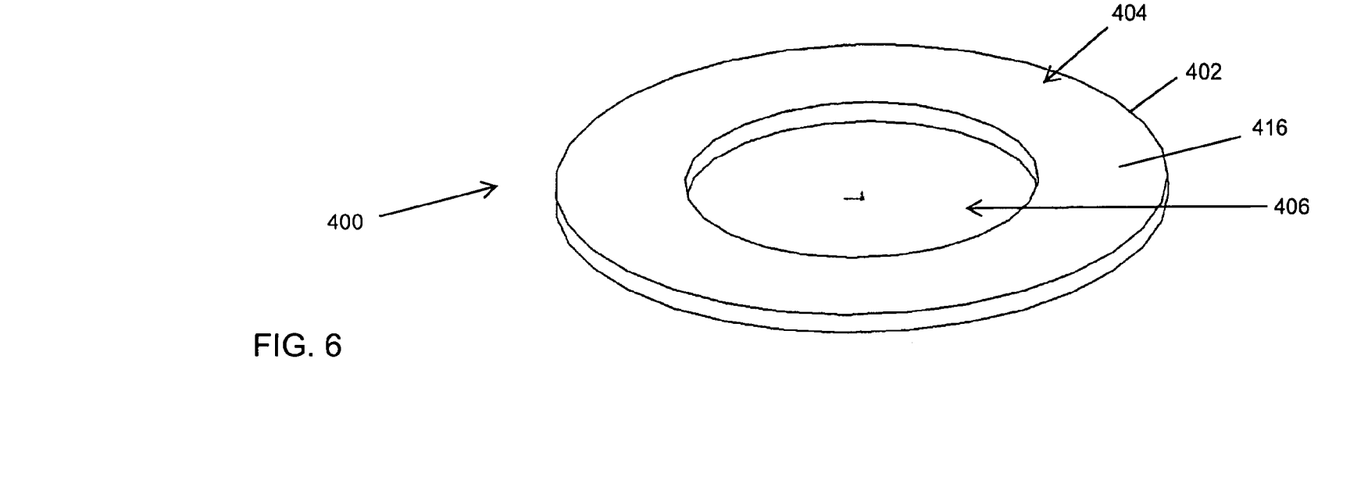
FIG. 6 is a perspective view of an exemplary embodiment of a therapeutic agent delivery device.
Figure 7:
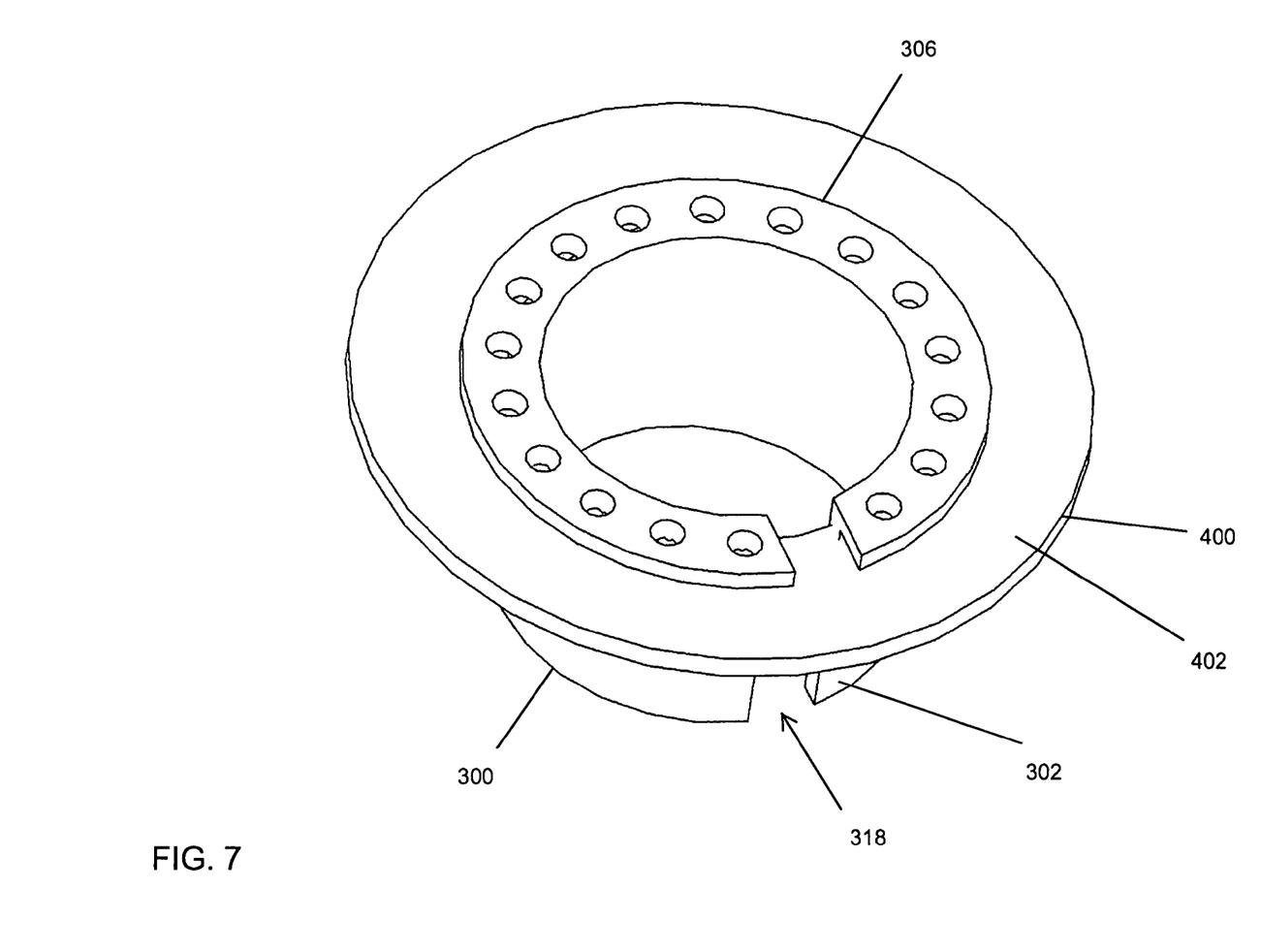
FIG. 7 is a perspective view of the exemplary embodiment of the therapeutic agent delivery device fitted on the guide.

FIG. 6 is a perspective view of an exemplary embodiment of a therapeutic agent delivery device 400 that could additionally or alternatively be used to deliver a drug or other therapeutic agent 416. The therapeutic agent delivery device 400 includes a member 402 with a surface 404 suitable for receiving the drug or therapeutic agent 416 and for delivering the therapeutic agent to living tissue. The member 402 could be constructed similarly to a washer. The surface 404 of the member 402 is formed with an aperture 406 sized for receiving the cylindrical body 302 of the guide 300. Sequential coatings of multiple drugs or therapeutic agents 416 could be applied to the member 402. Examples of drugs or therapeutic agents include antibiotics, growth factors, etc., and they could be released for a sustained period of time. The member 402 could be affixed to the guide 300 or to the suture anchor 100 during surgery or it could be preloaded thereon at the time of manufacture. The member 402 could be formed from a number of different materials. One option is to construct the member from a polymeric material, for example. FIG. 7 is a perspective view of showing the member 402 of the therapeutic agent delivery device 400 fitted on the cylindrical body 302 of the guide 300. The slot 318 formed in the cylindrical body 302 can also been seen.

Figure 8:
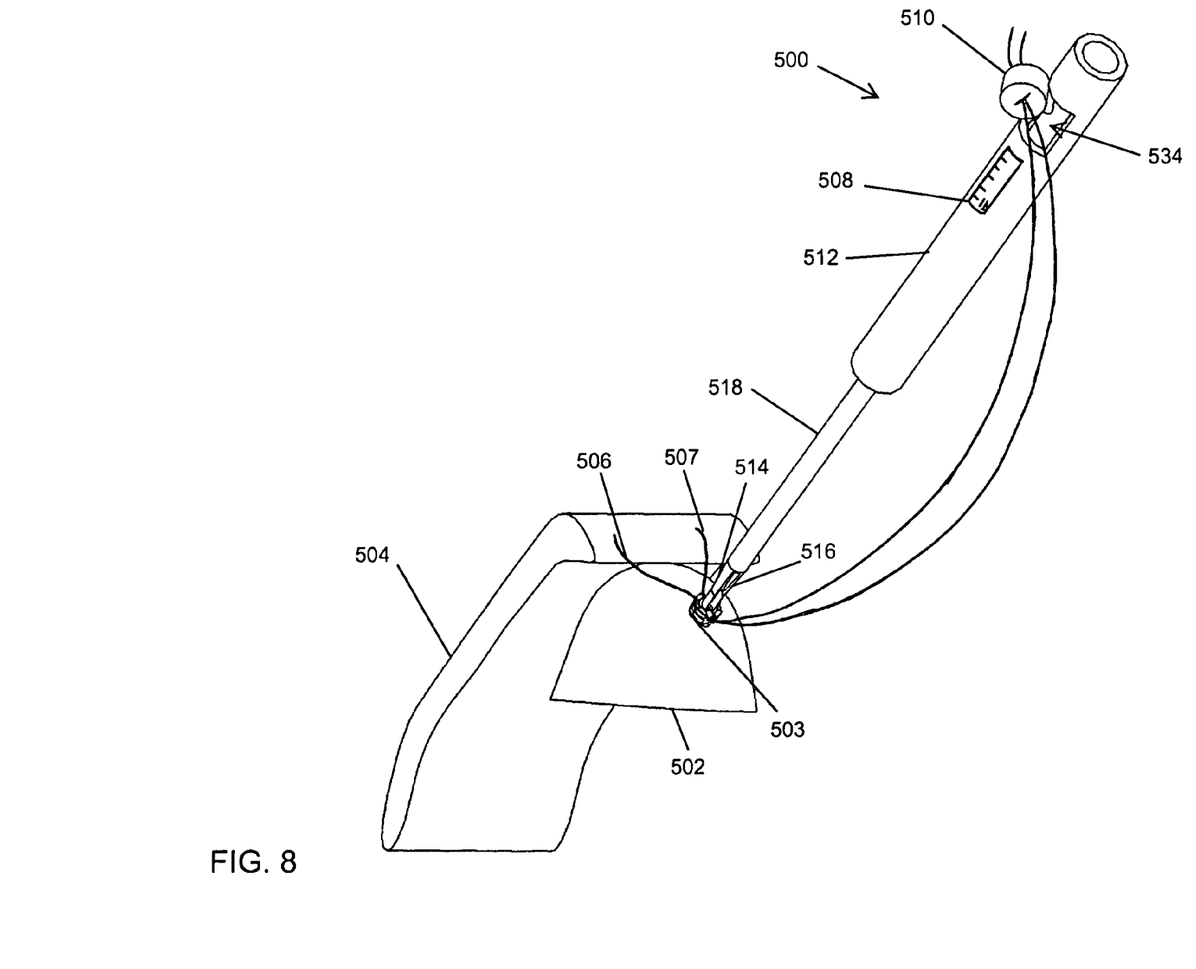
FIG. 8 is a perspective view of a first exemplary embodiment of a suture anchor delivery tool inserting a suture anchor into a bone.

FIG. 8 is a perspective view of a first exemplary embodiment of a suture anchor delivery tool 500. The suture anchor delivery tool 500 is shown inserting the suture anchor 100 into a hole 503 that has been formed in a bone 502. The hole 503 is specifically formed to receive the suture anchor 100 and to securely hold the suture anchor 100 therein. The bone could be the bone of a human or of an animal. In this example, two suture strands 506, 507 are first attached to living tissue 504, for example, a ligament or a tendon, which will be re-attached to the bone 502. Then the suture strands 506, 507 are routed through the passage 132 (See FIG. 2) of the suture anchor 100. Although not required and not specifically shown in FIG. 8, after the hole 503 has been formed, the guide 300 (FIG. 5) can be inserted into the hole 503 to mark the location of the hole 503. The therapeutic agent delivery device 400 could also be placed on the guide 300 as shown in FIG. 7. If the radiopacity of the guide 300 has been enhanced with the second material 314 (FIG. 5), an imaging procedure may be used if necessary to locate the guide 300 and the hole 503. After the hole 503 is located, the suture anchor delivery tool 500 is used to insert the suture anchor 100 into the hole 503 as shown in FIG. 8.

FIG. 8 generally shows that the first exemplary embodiment of the suture anchor delivery tool 500 includes a handle portion 512, and a plurality of prongs 514, 516 that extend from the handle portion 512. In this example, an intermediate hollow cylindrical member 518, which extends from the handle portion 512, is constructed with the plurality of prongs 514, 516.

Figure 9:
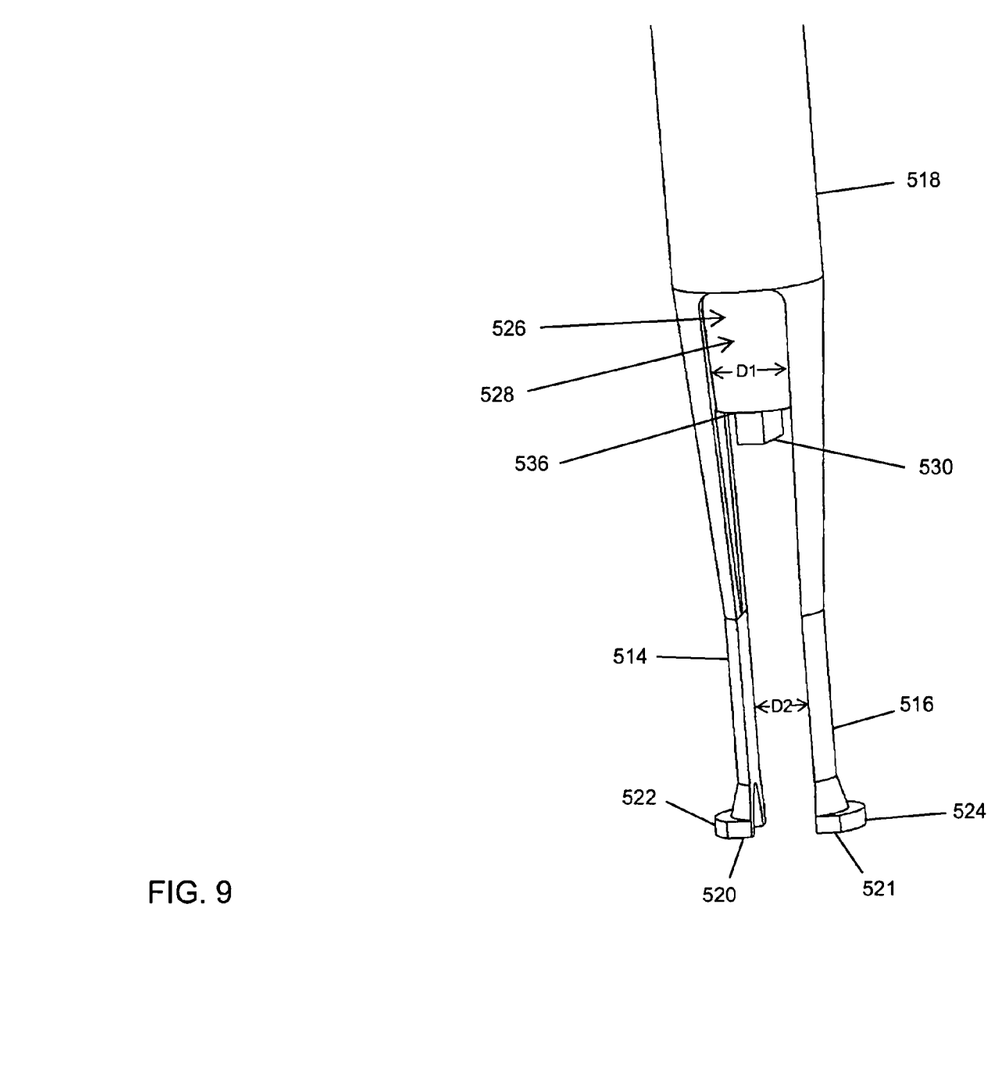
FIG. 9 is an enlarged perspective view of the lower portion of the first exemplary embodiment of the suture anchor delivery tool.

FIG. 9 is an enlarged perspective view of the lower portion of the first exemplary embodiment of the suture anchor delivery tool 500. FIG. 9 more clearly shows the plurality of prongs 514, 516 extending from the hollow cylindrical member 518. In this example, two prongs 514, 516 are shown however, more prongs could be constructed. Each one of the two prongs 514, 516 includes an end 520, 521 with a protuberance 522, 524 that is shaped, sized, and configured to secure the suture anchor 100. The protuberances 522, 524 are configured to be inserted into the opposing apertures 148, 149 (FIG. 3) that are formed in the suture anchor body 102 of the suture anchor 100 (FIG. 3). As will be explained below, after being fitted into the apertures 148, 149, the protuberances 522, 524 will then be pushed outward to tightly mate with the apertures 148, 149 (FIG. 3).

Still referring to FIG. 9, it is seen that the distance D1 between the prongs 514, 516 at the portion of the prongs 514, 516 that is remote from the ends 520, 521 is slightly greater than the distance D2 between the prongs 514, 516 at the portion of the prongs 514, 516 that is closer to the ends 520, 521. The suture anchor delivery tool 500 includes an actuating member 528 that is formed as an inner cylindrical member 526 and that could be a shaft. The actuating member 528 is formed with an outer diameter that is matched to the distance D1 between the prongs 514, 516 at the portion that is remote from the ends 520, 521. The actuating member 528 is attached to the actuator button 510 (FIG. 8), either directly or through an intermediate piece or pieces. Referring back to FIG. 8, a non-illustrated slot extends longitudinally down the handle portion 512 in a direction toward the suture anchor 100. This slot allows the actuator button 510 to be pushed toward the suture anchor 100. Referring again to FIG. 9, as the actuator button 510 is pushed toward the suture anchor 100 and likewise toward the ends 520, 521 of the prongs 514, 516, the outer diameter of the actuating member 528 pushes the prongs 514, 516 apart so that the protuberances 522, 524 move further apart.

Figure 10:
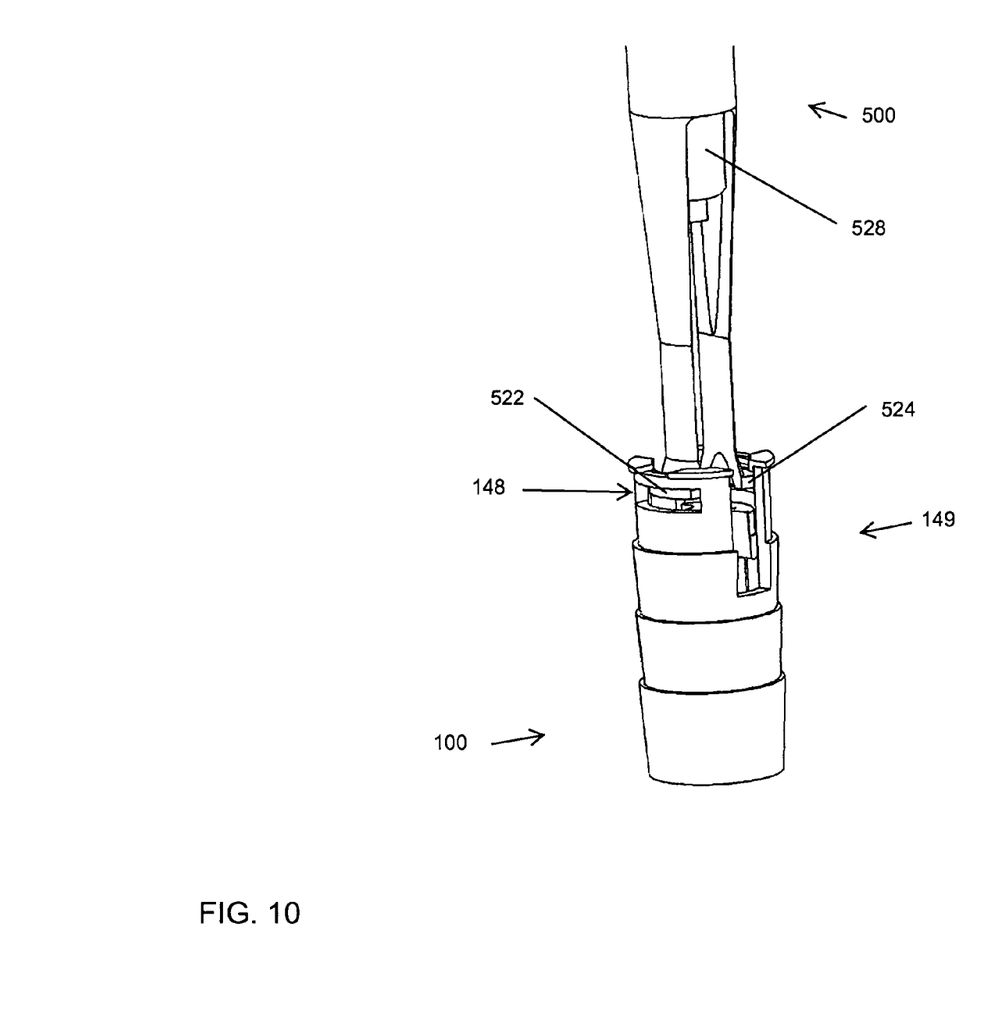
FIG. 10 is a perspective view of the first exemplary embodiment of the suture anchor delivery tool and the exemplary embodiment of the suture anchor.

The procedure used to lock the suture anchor 100 to the suture anchor delivery tool 500 begins with the actuator button 510 being placed in the upmost position in the non-illustrated slot. This brings the actuating member 528 to the upper position so that the prongs 514, 516 are not pushed apart. A biasing member or spring can be provided to bias the end 536 of the actuating member 528 in a rest or equilibrium state away from the ends 520, 521 of the prongs 514, 516. Since the prongs 514, 516 are not pushed apart in this state, the protuberances 522, 524 can easily be fitted in the apertures 148, 149 that are formed in the suture anchor body 102 of the suture anchor 100 as shown in FIG. 10. After the protuberances 522, 524 are fitted in the apertures 148, 149, the actuator button 510 (FIG. 8) is moved in the slot in the direction toward the suture anchor 100 and likewise toward the ends 520, 521 of the prongs 514, 516. This moves the actuating member 528 toward the ends 520, 521 of the prongs 514, 516, and moves the protuberances 522, 524 outward so that they are firmly locked in the apertures 148, 149. This causes the suture anchor 100 to be securely held by the suture anchor delivery tool 500.

FIG. 9 shows that the suture anchor delivery tool 500 may also include a structure 530 that is configured to mate with the turning device 152 (FIG. 1) of the suture anchor 100. This structure 530 serves as a key and could, for example, be implemented as a recess or as a projection. In this example, however, the structure is implemented as a projection 532 that is sized and shaped to correspond with the shape and size of the recess that is used to implement the turning device 152 of the suture anchor 100 shown in FIG. 1. FIG. 8 shows that the handle portion 512 is formed with an aperture 534 that allows the actuator button to be moved or rotated around the circumference of the handle portion 512. The aperture 534 preferably allows the actuator button to be rotated 180 degrees around the circumference of the handle portion 512. This rotational movement likewise rotates the actuating member 528 and accordingly rotates the structure 530.

As the actuating member 528 is moved longitudinally toward the ends 520, 521 of the prongs 514, 516 to move the protuberances 522, 524 outward, the structure 530 is mated with the turning device 152 of the suture anchor 100. Then the actuating member 528 can be rotated or turned to turn the turning device 152 and move the projection 136 into and out of the disengagement channel 146 (FIG. 1).

As the end 536 of the actuating member 528 is longitudinally moved further and further past the ends 520, 521 of the prongs 514, 516 via the actuator button 510, the end of the actuating member 528 pushes the top surface 122 of the securing member 104 downward so that the projection 136 of the suture anchor body 102 enters subsequent recesses 134 formed in the securing member 104. When the first clamping surface 114 and the second clamping surface 124 (FIG. 1) are positioned such that the desired force is applied to the suture strands 506, 507 (FIG. 8), the actuating member 528 is no longer moved downward. The first clamping surface 114 and the second clamping surface 124 are then fixed in a clamping position that is set by the location of the projection 136 in a particular one of the recesses 134. If too much force has been applied, the fixed clamping position can be unlocked or released by rotating the actuator button 510 to rotate the structure 530 and the turning device 152 and to bring the projection 136 into the disengagement channel 146.

Referring again to FIG. 8, it is seen that the suture anchor delivery tool may include a tension indicator 508 that indicates the tension being applied to the suture strands 506, 507, an actuator button 510 with a through-hole 506 for receiving the suture strands 506, 507, and a non-illustrated tension sensing mechanism for sensing the tension being applied to the suture strands 506, 507. The tension sensing mechanism could be, for example, a spring with a known spring constant, and the tension indicator 508 could be mechanically constructed and calibrated in accordance with the spring constant. In this case, one end of the spring could be attached to the actuator button 510 and the other end of the spring could be attached to the mechanically constructed tension indicator 508. As the tension on the suture strands 506, 507 is increased, the actuator button 510 is correspondingly pulled towards the suture anchor 100, which also correspondingly loads the spring and causes the tension indicator 508 to indicate the tension. Alternatively, the tension indicator 508 and the tension sensing mechanism could be electronically constructed.

Figure 11:
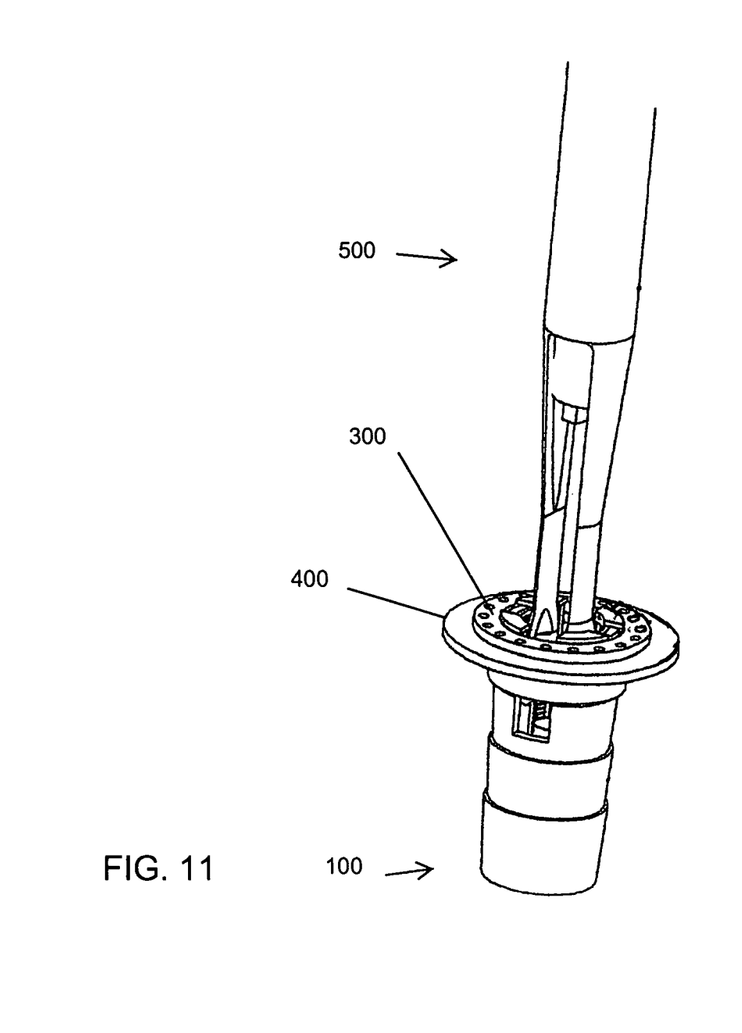
FIG. 11 is a perspective view of the exemplary embodiments of the suture anchor delivery tool, the suture anchor, the guide, and the therapeutic drug delivery device.

FIG. 11 is a perspective view showing the cooperation between the exemplary embodiments of the suture anchor delivery tool 500, the suture anchor 100, the guide 300, and the therapeutic drug delivery device 400.

Figure 12:
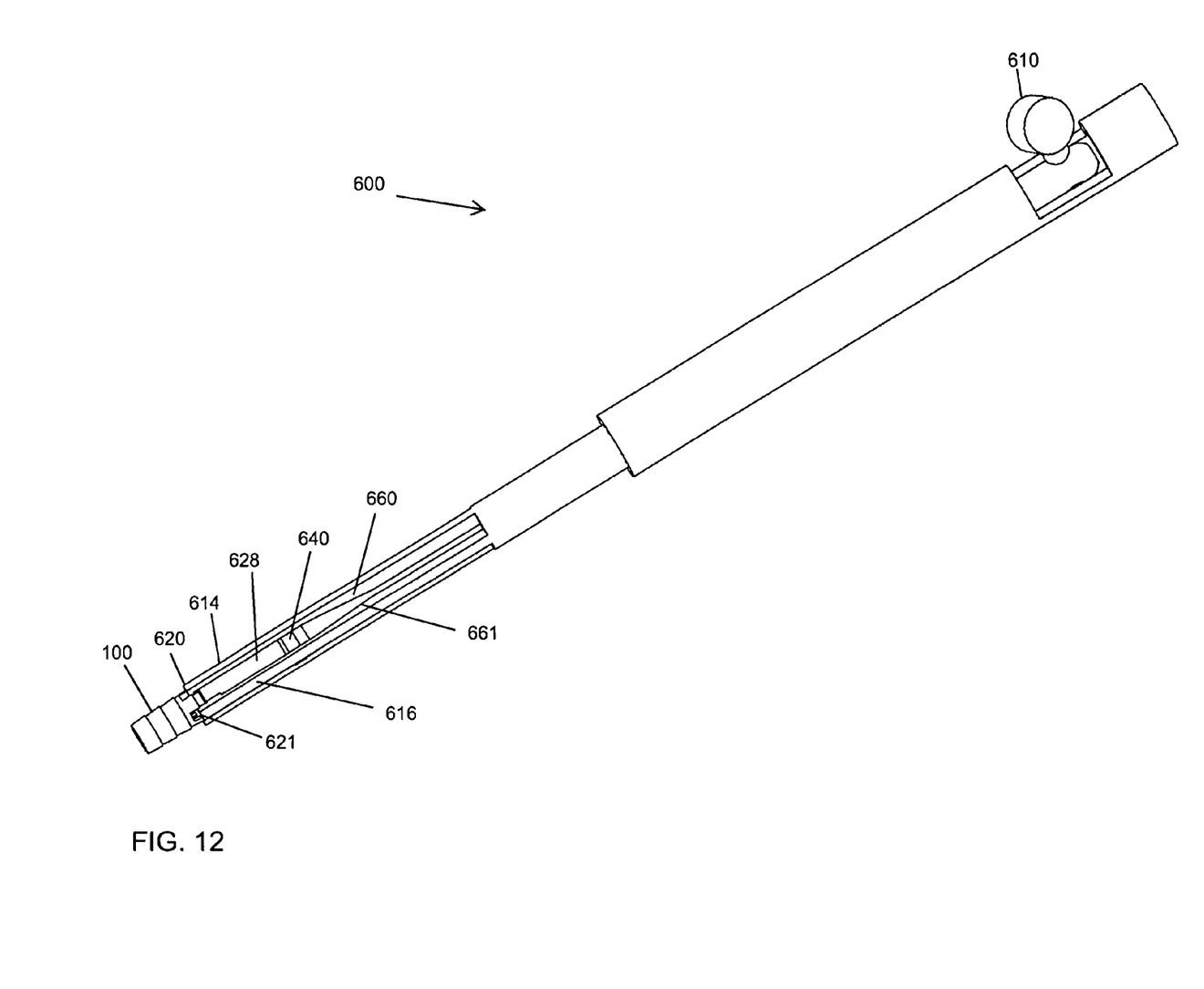
FIG. 12 is a perspective view of a second exemplary embodiment of a suture anchor delivery tool.
Figure 13:
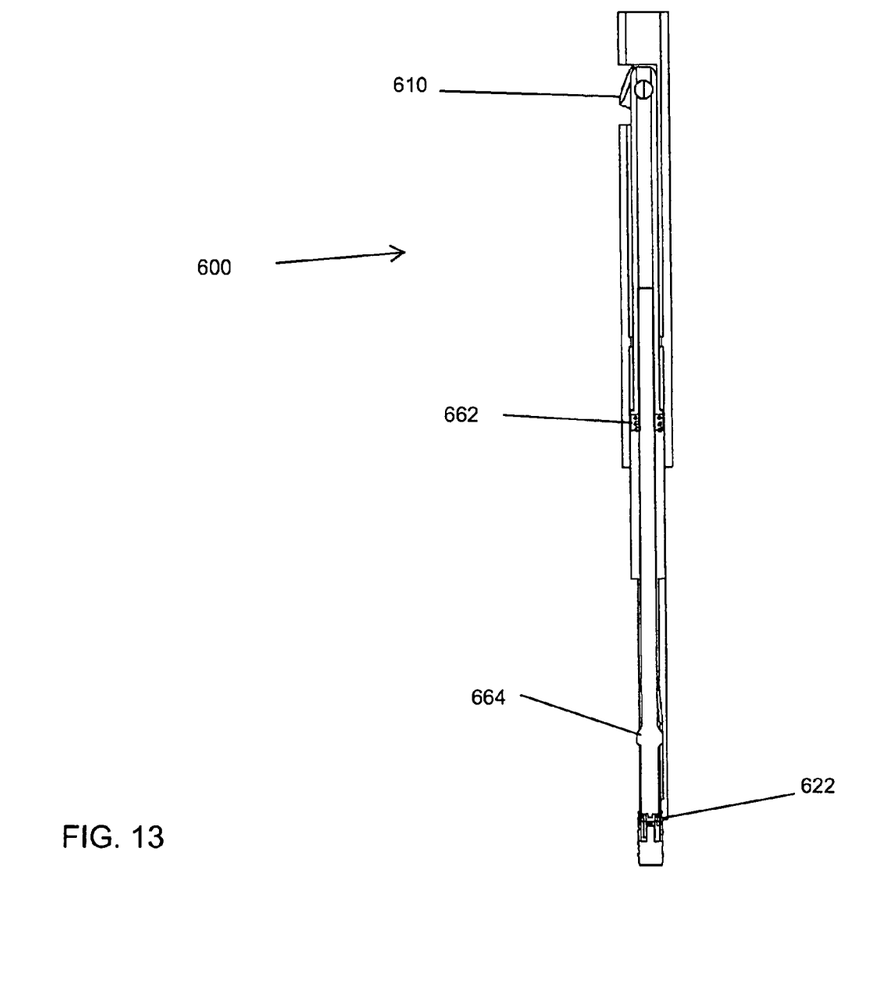
FIG. 13 is another view of a second exemplary embodiment of a suture anchor delivery tool.

FIG. 12 is a perspective view of a second exemplary embodiment of a suture anchor delivery tool 600, which is constructed similarly to the first exemplary embodiment except for the differences noted below. The suture anchor delivery tool 600 is constructed with a plurality of prongs 614, 616 that are constructed with protuberances 622 that are directed inward as shown in FIG. 13. The inwardly extending protuberances 622 are constructed to enter the apertures 148, 149 (FIG. 1) of the suture anchor body 102 from outside the suture anchor body 102 rather than from the interior of the suture anchor body 102 as is the case with the first exemplary embodiment of the suture anchor delivery tool 500. The prongs 614, 616 are constructed to be securely locked into the apertures 148, 149 (FIG. 1) of the suture anchor body 102. This is accomplished by making the distance between the prongs 614, 616 near the ends 620, 621 larger than the distance between the prongs 614, 616 remote from the ends 620, 621. When the actuating member 628 is in its upward position, the cam surface 664 of the actuating member 628 pushed against the surfaces 660, 661 of the prongs 614, 616. Since the surfaces 660, 661 are closer together than the remote portions of the prongs 614, 616, the cam surface of the actuating member 628 pushes the prongs 614, 616 apart, which correspondingly pushes the protuberances 622 apart so that they are not securely engaged with the apertures 148, 149 (FIG. 1) of the suture anchor body 102. A biasing member 662 or spring can be provided to bias the actuating member 628 in a rest or equilibrium state away from the ends 620, 621 of the prongs 614, 616.

When the actuator button 610 is used to move the actuating member 628 towards the ends 620, 621 of the prongs 614, 616, the cam surface 664 of the actuating member 628 enables the prongs 614, 616 to move into a state in which the prongs 614, 616 are biased inward and the protuberances 622 are biased inward to securely lock into the apertures 148, 149 (FIG. 1) of the suture anchor body 102.

We claim:

1. A suture anchor, comprising:
   a suture anchor body for placement in a bone, said suture anchor body formed with a cavity and a first clamping surface; and
   a securing member constructed to be at least partially received in said cavity of said suture anchor body, said securing member formed with a second clamping surface;

said suture anchor body and said securing member cooperating to define a passage between said first clamping surface and said second clamping surface for receiving at least one suture strand;

said suture anchor body and said securing member formed with cooperating engaging structures enabling a distance between said first clamping surface and said second clamping surface to be adjusted in predetermined increments to thereby adjust a width of said passage between said first clamping surface and said second clamping surface;

said cooperating engaging structures holding said first clamping surface and said second clamping surface in a plurality of fixed predefined positions relative to each other;

said cooperating engaging structures include a plurality of recesses formed in one of said suture anchor body and said securing member, said cooperating engaging structures also including a projection extending from the other one of said suture anchor body and said securing member, said projection constructed to be received in said plurality of recesses; and wherein the one of said suture anchor body and said securing member, which is formed with said plurality of recesses, is also formed with a disengagement channel longitudinally extending through said plurality of recesses; and said disengagement channel releases said securing member when said projection is moved into said disengagement channel.

2. The suture anchor according to claim 1, wherein:
said securing member is constructed to be completely received in said cavity of said suture anchor body; and
said suture anchor body includes a retaining flange constructed to retain said securing member in said suture anchor body when said projection is moved into said disengagement channel and said securing member is released.

3. The suture anchor according to claim 1, wherein:
said securing member is constructed to be completely received in said cavity of said suture anchor body; and
said suture anchor body includes a retaining flange constructed to retain said securing member in said suture anchor body when said cooperating engaging structures are disengaged.

4. The suture anchor according to claim 1, further comprising a biasing member applying a force biasing said securing member away from said suture anchor body.

5. The suture anchor according to claim 1, wherein: said plurality of recesses are formed in said suture anchor body and said projection extends from said securing member;

said projection of said securing member is constructed to be received in said plurality of recesses formed in said suture anchor body;
said suture anchor body is also formed with said disengagement channel longitudinally extending through said plurality of recesses;
said disengagement channel releases said securing member when said projection is moved into said disengagement channel; and
said securing member is formed with a turning device enabling said securing member to be turned such that said projection is moved into and out of said disengagement channel, said turning device having a shape designed for mating with a complementary shaped device of a tool.

6. The suture anchor according to claim 1, wherein:
said suture anchor body and said securing member extend in a longitudinal direction, and said securing member is formed with an indented suture passage extending in the longitudinal direction; and
said suture passage is constructed for routing the at least one suture strand away from said suture anchor body and said securing member and for preventing contact between the at least one suture strand and the bone when said suture anchor body is placed in the bone.

7. The suture anchor according to claim 1, wherein said suture anchor body includes an end portion formed with at least two opposing apertures for interlocking with a suture anchor delivery tool.

8. The suture anchor according to claim 1, wherein at least said suture anchor body includes at least one agent selected from the group consisting of:
a bonding agent for cells,
a bonding agent for molecules,
a bonding agent for proteins,
an agent serving as a moisture and chemical barrier,
an agent that enables dry lubricity, and
an agent that prevents fluid conduction of galvanic charge.

9. The suture anchor according to claim 1, wherein said plurality of fixed predefined positions is a plurality of discrete positions.

10. The suture anchor according to claim 1, wherein said cooperating engaging structures define a ratchet.

11. The suture anchor according to claim 1, wherein said securing member has a top surface with at least two suture passages formed therein.

12. The suture anchor according to claim 1, wherein:
said projection is moveable through said disengagement channel without being received in said plurality of recesses.

* * * * *